(12) United States Patent
Lee et al.

(10) Patent No.: US 9,030,215 B2
(45) Date of Patent: May 12, 2015

(54) REAL-TIME, LABEL-FREE DETECTION OF NUCLEIC ACID AMPLIFICATION IN DROPLETS USING IMPEDANCE SPECTROSCOPY AND SOLID-PHASE SUBSTRATE

(71) Applicants: Abraham P. Lee, Irvine, CA (US); Javier Lopez-Prieto, Cambridge, MA (US); Robert Lin, Berkeley, CA (US); Mindy Simon, Irvine, CA (US); Nick Martin, Irvine, CA (US)

(72) Inventors: Abraham P. Lee, Irvine, CA (US); Javier Lopez-Prieto, Cambridge, MA (US); Robert Lin, Berkeley, CA (US); Mindy Simon, Irvine, CA (US); Nick Martin, Irvine, CA (US)

(73) Assignee: The Regents of the University of California Corporation, Oakland, CA (US)

( * ) Notice: Subject to any disclaimer, the term of this patent is extended or adjusted under 35 U.S.C. 154(b) by 247 days.

(21) Appl. No.: 13/573,750

(22) Filed: Oct. 3, 2012

(65) Prior Publication Data

US 2013/0154671 A1 Jun. 20, 2013

Related U.S. Application Data

(60) Provisional application No. 61/543,203, filed on Oct. 4, 2011.

(51) Int. Cl.
*G01R 27/02* (2006.01)
*C12Q 1/68* (2006.01)

(52) U.S. Cl.
CPC ............... *G01R 27/02* (2013.01); *C12Q 1/686* (2013.01)

(58) Field of Classification Search
CPC ....................................................... G01R 27/01
See application file for complete search history.

(56) References Cited

U.S. PATENT DOCUMENTS

| | | | |
|---|---|---|---|
| 8,613,889 B2 * | 12/2013 | Pollack et al. | 422/68.1 |
| 2012/0021423 A1 * | 1/2012 | Colston et al. | 435/6.12 |
| 2013/0293246 A1 * | 11/2013 | Pollack et al. | 324/671 |
| 2014/0154695 A1 * | 6/2014 | Miller et al. | 435/6.12 |

* cited by examiner

*Primary Examiner* — Jermele M Hollington

(57) ABSTRACT

A method for detecting presence of nucleic acid amplification in a test droplet. A set of detection electrodes are provided in contact with a fluidic channel. The test droplet is provided in vicinity of the detection electrodes through the fluidic channel. An alternate current (AC) power at a first frequency is applied across the set of detection electrodes. A first measurement value that reflects electrical impedance of the test droplet at the first frequency is obtained. This value is compared with a corresponding reference value, wherein the corresponding reference value is obtained by measuring a reference droplet containing known amplified nucleic acid or known unamplified nucleic acid at the first frequency. The presence of amplified nucleic acid in the test droplet is thus determined based on the comparison.

22 Claims, 7 Drawing Sheets

| | % correct, DNA amplified | % correct, DNA not amplified |
|---|---|---|
| Frequency 1 | 94.7 | 100 |
| Frequency 1 | 94.7 | 100 |
| Frequency 1 | 94.7 | 100 |
| Frequency 1 | 94.7 | 100 |
| Freq 1 + Freq 2 + Freq 4 | 100 | 100 |

Fig. 6

REAL-TIME, LABEL-FREE DETECTION OF NUCLEIC ACID AMPLIFICATION IN DROPLETS USING IMPEDANCE SPECTROSCOPY AND SOLID-PHASE SUBSTRATE

The present application claims the benefit of priority of U.S. provisional application (U.S. patent application No. 61/543,203), entitled as "Real-time, label-free detection of nucleic acid amplification in droplets using impedance spectroscopy and solid-phase substrate," filed on Oct. 4, 2011.

FIELD OF THE INVENTION

The present disclosure is generally related to detection and amplification of nucleic acid sequences. In particular, the disclosure relates to detection of nucleic acid amplification in droplets.

BACKGROUND OF THE INVENTION

Polymerase Chain Reaction (PCR) has been widely used to amplify a specific region of a DNA or RNA strand across several orders of magnitude, generating thousands to millions of copies of a particular DNA or RNA sequence. It has long been adopted as a standard procedure in the detection of nucleic acid targets due to the techniques' sensitivity and accuracy. Droplet microfluidics' ability to rapidly generate isolated reaction chambers serves as a convenient platform for the adaption of PCR. Because of the synergy, droplet PCR or digital PCR has garnered much research interest in recent years. Real-time PCR is a tool for DNA or RNA quantification that measures the accumulation of DNA or RNA product after each round of PCR amplification.

Conventionally, as a polymerase enzyme completes the complementary strand, a fluorescent label is release from a fluorescent probe, creating a fluorescent signal that is detectable optically. However, the need for fluorescent illumination as well as detection and the processing required to prepare fluorescent markers generally increases the cost of such systems.

There is a need to reduce the cost of detecting nucleic acid target. It would be advantageous to provide a method of PCR detection without the need for fluorescently labeled substrate. It would also be advantageous to provide a detection process feasible for real time detection of DNA or RNA amplification and high throughput integrated microfluidic platform.

SUMMARY OF THE INVENTION

Accordingly, embodiments of the present disclosure present a method to verify the completion of the reaction utilizing impedance-based detection by incorporating the technique of electrical impedance spectroscopy, eliminating the need for fluorescently labeled substrate.

In one embodiment of the present disclosure, a method for detecting presence of amplified nucleic acid in a test droplet comprises providing a set of detection electrodes in a fluidic channel, providing the test droplet in vicinity of the electrodes, applying an AC power across the electrodes at a first frequency, obtaining a first measurement value reflecting electrical impedance of the test droplet, comparing the measurement value with a corresponding reference value and determining presence of amplified nucleic acid in the test droplet based on the comparison. The corresponding reference value is obtained by measuring a reference droplet containing known amplified nucleic acid or known unamplified RNA at the first frequency.

In one embodiment of the present disclosure, the obtaining the first measurement value comprises using an impedance scope in combination with a current amplifier. In one embodiment, the first measurement value and reference value are peak-to-peak voltages derived from respective real time voltage-time plots in respective measuring periods. In one embodiments of the present disclosure, obtaining the first measurement value comprises a differential impedance measuring in a multi-frequency interrogation.

In one embodiment of the present disclosure, a system for detecting presence of nucleic acid amplification in a series of droplets comprising a fluidic channel, a set of detection electrodes in contact with the fluidic channel, an AC power supply operable to apply electrical powers across the set of electrodes at a plurality of known frequencies, an impedance measurement device operable to measure electrical impedance of each of said series of test droplets and a processor operable to compare measured electrical impedance of the test droplets with corresponding reference electrical impedance, and a processor operable to compare measured electrical impedance of each of said series of test droplets with corresponding reference electrical impedances. The corresponding reference electrical impedances are obtained by measuring a reference droplet at multiple known frequencies respectively. The corresponding reference droplet is of substantially the same size as the testing droplets and contains known amplified nucleic acid or known unamplified RNA at the first frequency.

In one embodiment of the present disclosure, method for detecting presence of nucleic acid amplification in a test droplet comprising: providing a set of detection electrode within a fluidic channel, providing said test droplet in vicinity of electrode, applying high frequency power across said set of detection electrodes at four different frequencies in sequence, measuring electrical impedances of the test droplet at the four frequencies by differential impedance measurements, comparing the measured electrical impedances with corresponding reference electrical impedances obtained by measuring a reference droplet at said four different frequencies respectively. The reference droplet is of substantially the same size as the testing droplet and contains known amplified nucleic acid or known unamplified nucleic acid, and determining the presence of amplified nucleic acid in the test droplet based on the comparison.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present disclosure is illustrated by way of example, and not by way of limitation, in the Figs. of the accompanying drawings and in which like reference numerals refer to similar elements.

FIG. 6 lists sample detection accuracy results achieved by one frequency interrogation and multiple frequency interrogation respectively in accordance with embodiments of the present disclosure.

DETAILED DESCRIPTION OF THE INVENTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, and components have not been described in detail as not to unnecessarily obscure aspects of the embodiments of the present invention.

Figure 1:
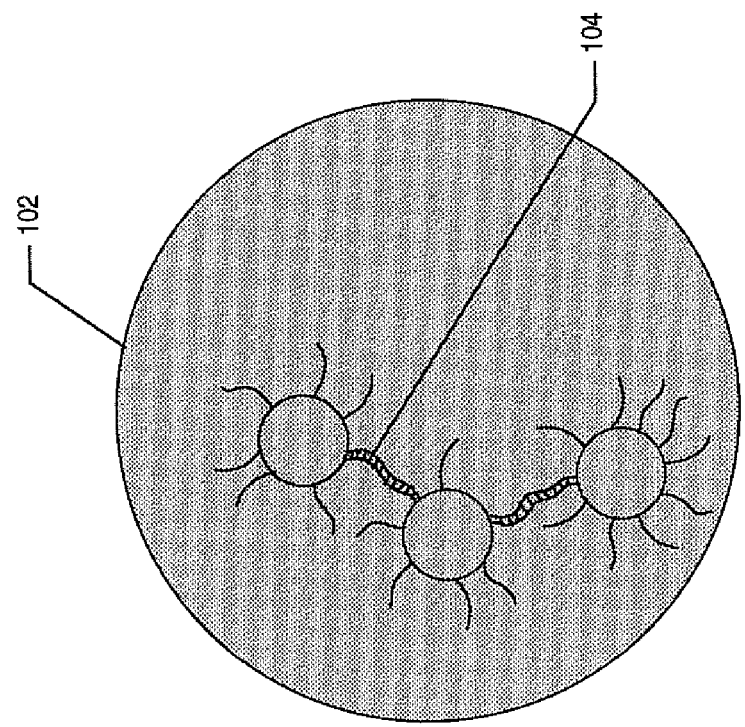
FIG. 1 schematically illustrates the underlying mechanism causing different electrical impedances in a droplet containing non-amplified DNA and a droplet containing amplified DNA.
Figure 1:
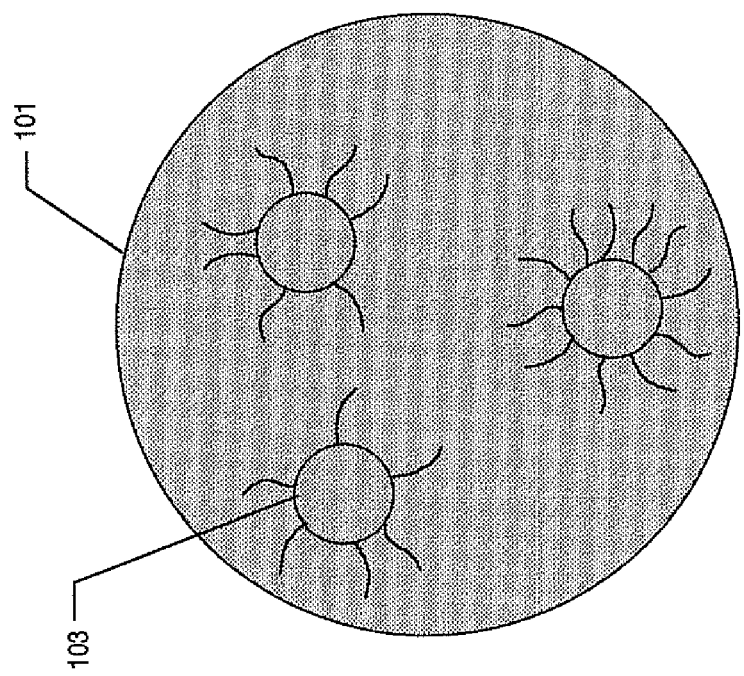

Real-Time, Label-Free Detection of Nucleic Acid Amplification in Droplets Using Impedance Spectroscopy and Solid-Phase Substrate Generally speaking, droplets containing amplified DNA or RNA present different electrical characteristics from droplets containing non-amplified DNA or RNA. The underlying mechanism is illustrated in FIG. 1. When a target DNA or RNA strand is not present in a droplet sample 101, nanoparticles 103 do not aggregate during thermocycling in a PCR process. In contrast, with the presence of the target DNA or RNA strand 104, primers 104 conjugated to nanoparticles 103 cause aggregation of the nanoparticles 103 in the PCR process. Thereby the electrical impedance of the droplet is changed, which can be measured as the droplet 102 is subject to a certain electrical field in a microfluidic channel. The measurement results, in turn, can be used to determine the presence of amplified DNA or RNA in the droplet.

Figure 2:
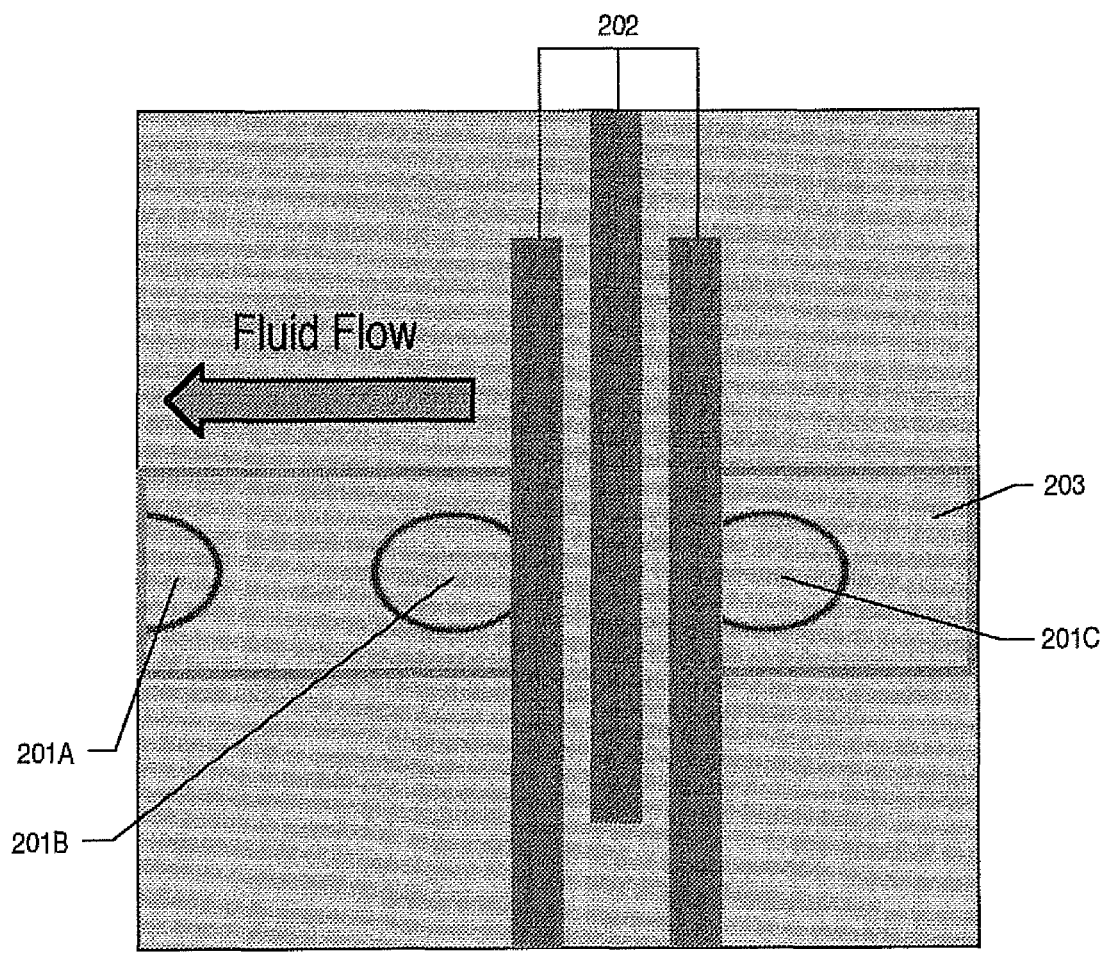
FIG. 2 illustrates a partial schematic configuration of a microfluidic device 200 implementing impedance spectroscopy on the droplets to detect presence of amplified DNA in the droplets in accordance with an embodiment of the present disclosure.

Referring to FIG. 2. FIG. 2 illustrates a schematic configuration of a microfluidic device 200 implementing impedance measurement on the droplets to detect presence of amplified DNA in the droplets in accordance with an embodiment of the present disclosure. The microfluidic device 200 comprises a microfluidic channel 203 and a set of detection electrodes 202 that are connected to a high frequency or radio frequency power supply for imposing an electrical field on the droplets 201A-201C flowing by. The detection electrodes 202 are spaced and disposed perpendicular to the fluid flow direction in this embodiment. In this embodiment, the set of electrodes 202 consists of 3 gold electrodes.

In some embodiments, differential impedance measurements are employed to determine the electrical impedance of each test droplet, in which an electrical field of a certain frequency is applied to a first two electrodes and then to a second two electrodes. In some embodiments, a common electrode may be shared in the two measurements. The measurements, including excitation signal generation, amplification and demodulation, may be achieved by utilizing an impedance spectroscope (not shown) in combination with a current amplifier (not shown), such as model HF2IS and HF2TA manufactured by Zurich Instruments.

Figure 3A:
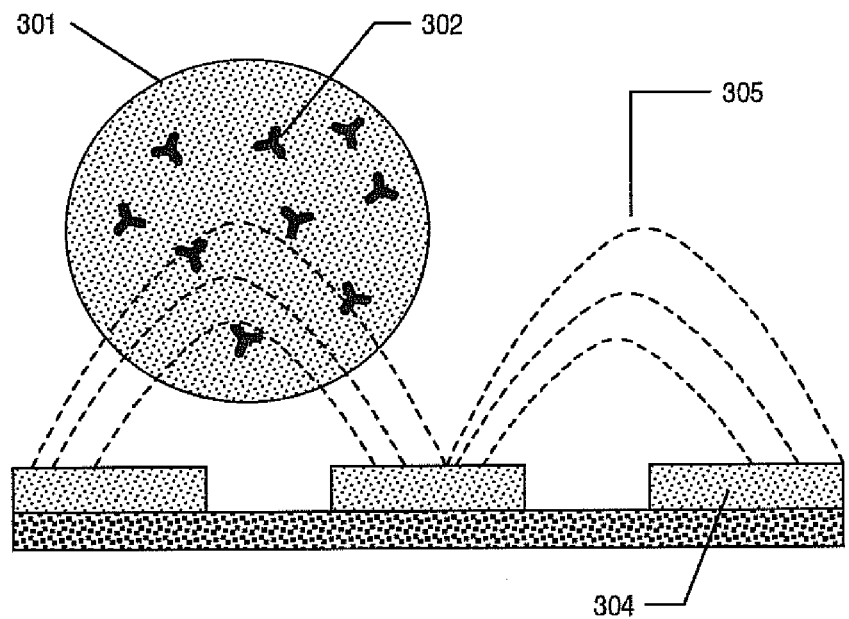
FIG. 3A illustrates a schematic view of a series of droplets containing unpolymerized DNA monomers flowing over the detection electrodes in accordance with an embodiment of the present disclosure.
Figure 3B:
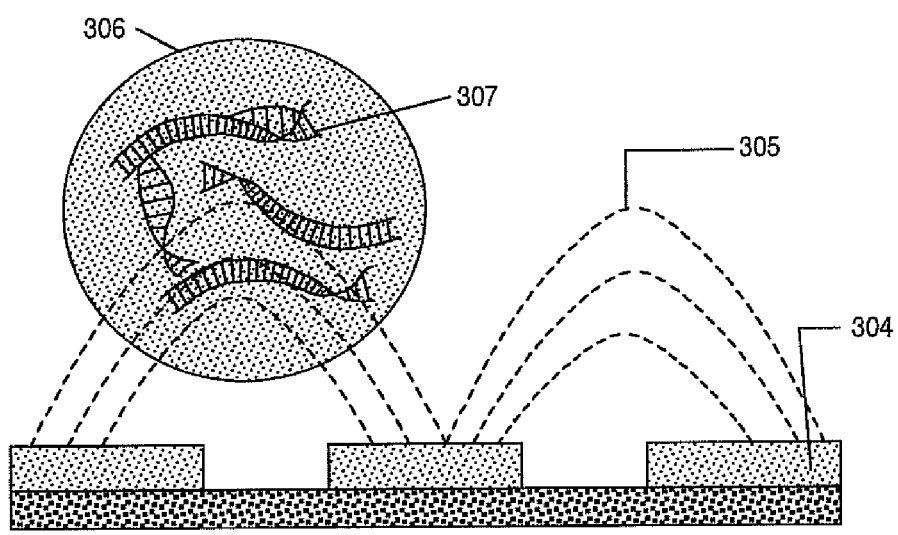
FIG. 3B illustrates a schematic view of a series of droplets containing polymerized DNA monomers flowing over the detection electrodes in accordance with an embodiment of the present disclosure.

FIG. 3A illustrates a schematic view of a series of droplets 303 containing unpolymerized DNA monomers 302 flowing over the detection electrodes 304 in accordance with an embodiment of the present disclosure. Also illustrated therein is an exploded view of a single droplet 301 containing unpolymerized DNA monomers 302. By comparison, FIG. 3B illustrates a schematic view of a series of droplets 305 containing polymerized DNA monomers 307 flowing over the detection electrodes 304 in accordance with an embodiment of the present disclosure. An exploded view of a single droplet 306 containing unpolymerized DNA monomers 307 is illustrated as well.

Figure 4:
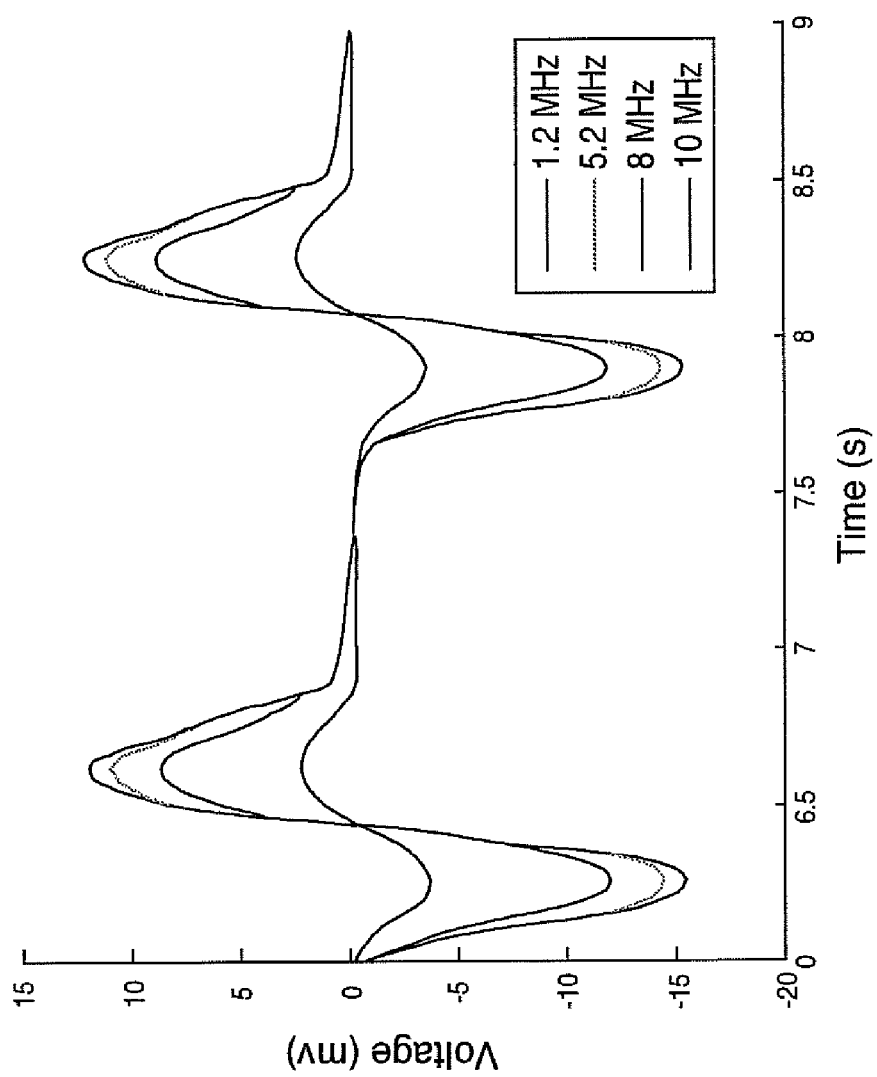
FIG. 4 shows sample voltage–time plots obtained from four-frequency measurement on two consecutive droplets in accordance with an embodiment of the present disclosure.

Referring to FIG. 4. When performing an impedance measurement at a certain excitation frequency on an individual droplet, the impedance spectroscope can produce a real time voltage–time plot. The amplitude of peak-to-peak voltage extracted from the real time plots reflects electrical impedance of the droplet. The peak-to-peak voltage obtained on the test droplet can then be compared with reference electrical impedance value. In some embodiments, the reference electrical impedance values are peak-to-peak voltages obtained from measuring reference droplets known to contain amplified DNA or non-amplified DNA respectively in a similar measuring context with the test droplet measurement, such as the size of the droplets, the frequency applied to the detection electrodes and the conditions of microfluidic channel. In some embodiments, the reference impedance value for a droplet containing non-amplified DNA is obtained by measuring a reference droplet that has not been subject to a PCR procedure. Thus, the presence of amplified DNA on the test droplet is determined based on the comparison.

Figure 5:
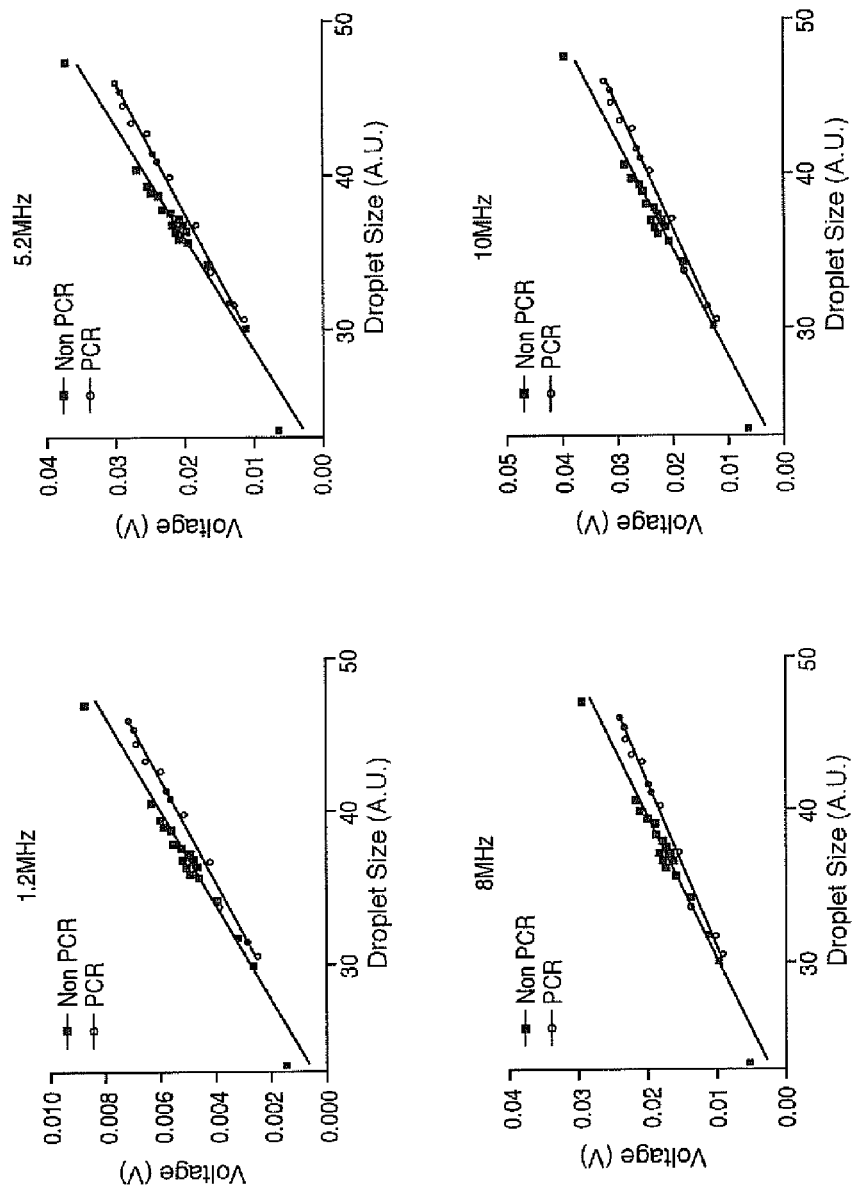
FIG. 5 are sample reference plots of peak-to-peak voltages obtained from measuring reference droplets of a variety of sizes at four frequencies in accordance with an embodiment of the present disclosure.

In some embodiments, a multiple-frequency interrogation scheme and subsequent demodulation can be performed on a single test droplet to determine the presence of amplified DNA for enhanced accuracy. FIG. 4 is sample voltage–time plots obtained from four-frequency measurement on two consecutive droplets in accordance with an embodiment of the present disclosure. The four excitation frequencies are 1.2 MHz, 5.2 MHz, 8 MHz and 10 MHz respectively in this embodiments. FIG. 5 are reference plots of peak-to-peak voltages obtained from measuring reference droplets of a variety of sizes at each of these four frequencies in accordance with an embodiment of the present disclosure. Each data point represents a single droplet. Linear fitting of the collected peak-to-peak voltage data creates reference curves. The curves show obvious differences in the voltage signals obtained from droplets containing amplified DNA and non-amplified DNA. These reference curves can subsequently be used as a predictor for DNA amplification in test droplets. In some other embodiments, measured electrical impedance can be independent of the sizes of the droplets, sparing the requirement for collecting reference values on different sizes of reference droplets.

FIG. 6 lists sample detection accuracy results achieved by one frequency interrogation and multiple frequency interrogation respectively in accordance with embodiments of the present disclosure. It shows that combining measurement results obtained from multiple frequencies provides enhanced discriminatory power in detecting droplets containing either amplified or non-amplified DNA in the droplets.

Figure 7:
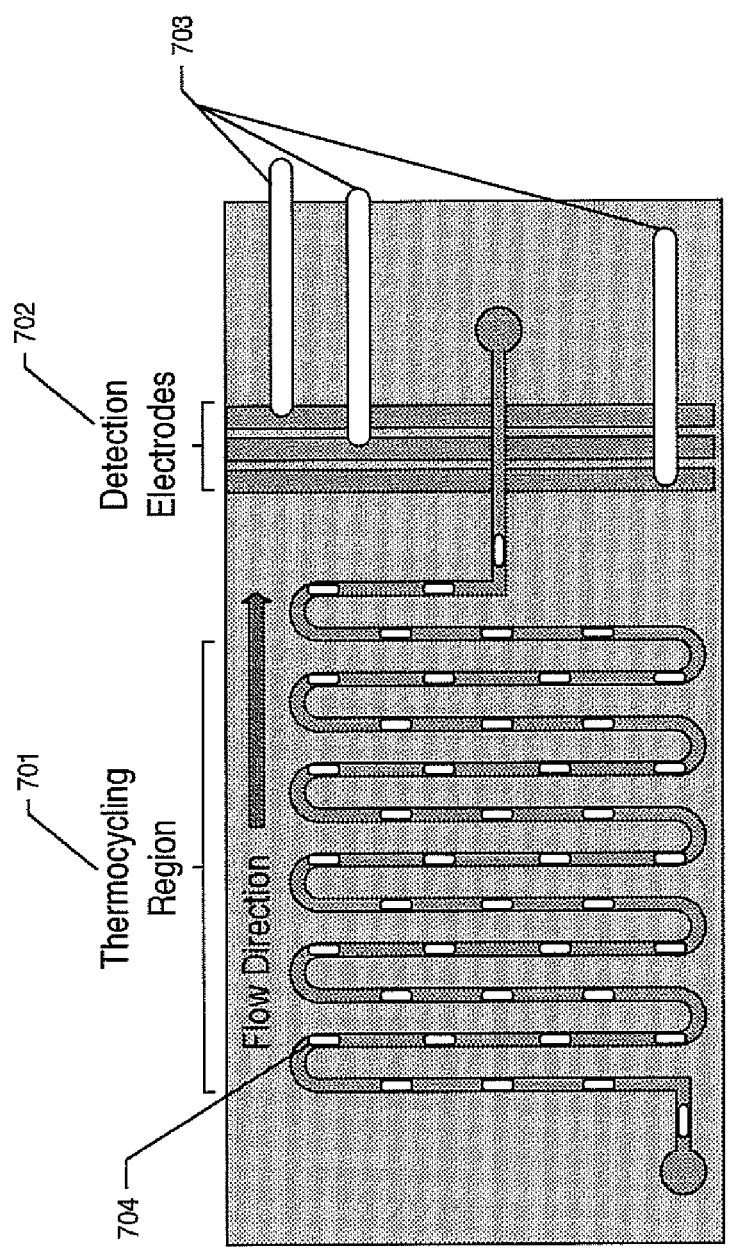
FIG. 7 illustrates a schematic view of a droplet-based PCR platform that incorporates impedance-based detection method in accordance with an embodiment of the present disclosure.

FIG. 7 illustrates a schematic view of a droplet based PCR platform that incorporates impedance-based detection method in accordance with an embodiment of the present disclosure. The platform comprises a thermocycling region 701 for the PCR process, a set of detection electrodes 702 and electrical contact pads 703. Test droplets 701 coming from the thermocycling region 701 flow over the detection electrodes 702 through a fluidic channel 704 in sequence. The detection electrodes are coupled with a current amplifier and an impedance spectroscope which provide measurement mechanism for electrical impedance of each droplet in the fluidic channel 704. In some embodiments, the measurement data can be input to a computing device equipped with suitable hardware and software programs substantially in real-time and are processed in a manner compatible with an embodiment of present disclosure. In some embodiments, the platform is made part of an automated system and thereby made suitable for performing label-free DNA detection at high efficiency.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for detecting presence of nucleic acid amplification in a test droplet, the method comprising:
providing a set of detection electrodes in contact with a fluidic channel;
providing the test droplet in vicinity of said set of detection electrodes through the fluidic channel;
applying an alternating current (AC) power at a first frequency across said set of detection electrodes;
obtaining a first measurement value reflecting electrical impedance of the test droplet at said first frequency;
comparing said first measurement value reflecting electrical impedance of the test droplet with a first corresponding reference value, wherein said first corresponding reference value is obtained by measuring a reference droplet containing known amplified nucleic acid or known unamplified nucleic acid in suspension within said reference droplet at said first frequency; and
determining presence of amplified nucleic acid in suspension within the test droplet based on said comparing.

2. The method as described in claim 1, wherein said set of electrodes comprises three planar gold electrodes.

3. The method as described in claim 1, wherein said reference droplet contains amplified DNA or RNA as a result of PCR.

4. The method as described in claim 1, wherein said fluidic channel comprises a constriction region over said set of detection electrodes.

5. The method as described in claim 1, wherein both said first measurement value and said first corresponding reference value are peak-to-peak voltages in respective measuring periods and derived by utilizing an impedance scope in combination with an current amplifier.

6. The method as described in claim 5, wherein said peak-to-peak voltages are derived from respective real time voltage-time plots produced by said impedance scope in combination with said current amplifier.

7. The method as described in claim 6,
wherein said set of detection electrodes comprise two groups of electrodes wherein the two groups share a common excitation or detection electrode; and
wherein obtaining said first measurement value further comprises a differential impedance measurement conducted across said two groups of detection electrodes respectively.

8. The method as described in claim 7 further comprising:
performing at least three additional differential impedance measurements on the test droplet at three additional frequencies conducted across said set of detection electrodes;
comparing peak-to-peak voltage values obtained from said three additional measurements with three corresponding reference values respectively, wherein said three corresponding reference values are obtained by measuring said reference droplet at said three additional frequencies respectively; and
determining presence of amplified nucleic acid in suspension within the test droplet by incorporating results from said three additional measurements.

9. The method as described in claim 8, wherein said first frequency and said additional frequencies are equal to 1.2 MHz, 5.2 MHz and 8 MHz and 10 MHz respectively.

10. The method as described in claim 6, wherein determining the presence of amplified nucleic acid in the test droplet is performed at substantially the same time as obtaining said first measurement value and said performing three additional differential impedance measurements.

11. The method as described in claim 1, where in the test droplet remains stationary while obtaining said first measurement value.

12. The method as described in claim 1, wherein said first measurement value reflecting electrical impedance of the test droplet is independent of the droplet size.

13. The method as described in claim 1 further comprising comparing said first measurement value reflecting electrical impedance of the test droplet with a second reference value obtained by measuring another reference droplet containing known non-amplified nucleic acid at the same AC power with said first frequency.

14. The method as described in claim 1, wherein said first measurement value reflecting electrical impedance is a magnitude of electrical impedance or real, or imaginary electrical impedance.

15. A system for detecting presence of nucleic acid amplification in a series of droplets, the system comprising:

a fluidic channel providing a plurality of test droplets of known sizes;

a set of detection electrodes disposed in contact with the fluidic channel;

an AC power supply operable to apply electrical powers across the set of detection electrodes at a plurality of known frequencies;

an impedance measurement device operable to measure electrical impedance of each of said series of test droplets; and a processor operable to compare measured electrical impedance of each of said series of test droplets with corresponding reference electrical impedances and to determine presence of nucleic acid amplification in suspension within each of said series of test droplets based on comparison, wherein the corresponding reference electrical impedances are obtained by measuring a reference droplet at said plurality of known frequencies respectively, and wherein the corresponding reference droplet is of substantially the same size as the testing droplets and contains known amplified nucleic acid or known non-amplified nucleic acid in suspension within said reference droplet.

16. The system described as in claim 15 further comprising a thermocycling region for implementing PCR on said plurality of test droplets.

17. The system described as in claim 15 wherein the impedance measurement device comprises an impedance scope in combination with a current amplifier.

18. The system described as in claim 15 wherein the AC power supply is capable to supply AC powers to the set of electrodes at frequencies from 100 Hz to 50 MHz.

19. The system described as in claim 15 wherein the processor is capable of determining the presence of amplified nucleic acid in each of the test droplet in substantially real time based on the comparison between electrical impedances of said series of test droplets with corresponding reference electrical impedances.

20. A method for detecting presence of nucleic acid amplification in a test droplet, the method comprising:

providing a set of detection electrode within a fluidic channel, providing said test droplet in vicinity of said set of electrodes through the fluidic channel;

applying high frequency power across said set of detection electrodes at four different frequencies in sequence;

measuring electrical impedances of the test droplet at said four frequencies by differential impedance measurements across said detection electrodes;

comparing the measured electrical impedances with corresponding reference electrical impedances obtained by measuring a reference droplet at said four different frequencies respectively, wherein the reference droplet is of substantially the same size as the testing droplet and contains known amplified nucleic acid or known unamplified nucleic acid;

determining the presence of amplified nucleic acid in suspension within the test droplet based on the comparison.

21. The method as described in claim 1, wherein said test droplet comprises solid phase particles operable for enhancing electrical impedance signals of said test droplet during said obtaining said first measurement value.

22. The method as described in claim 21, wherein said solid phase particles comprise nanoparticles.

* * * * *